US009642540B2

(12) United States Patent
Kinoshita et al.

(10) Patent No.: US 9,642,540 B2
(45) Date of Patent: May 9, 2017

(54) BLOOD PRESSURE MEASUREMENT DEVICE

(71) Applicants: Hiroyuki Kinoshita, Kyoto (JP); Chisato Uesaka, Kyoto (JP); Yukiya Sawanoi, Nara (JP)

(72) Inventors: Hiroyuki Kinoshita, Kyoto (JP); Chisato Uesaka, Kyoto (JP); Yukiya Sawanoi, Nara (JP)

(73) Assignee: OMRON HEALTHCARE Co., Ltd., Kyoto (JP)

( * ) Notice: Subject to any disclaimer, the term of this patent is extended or adjusted under 35 U.S.C. 154(b) by 1139 days.

(21) Appl. No.: 13/751,246

(22) Filed: Jan. 28, 2013

(65) Prior Publication Data

US 2013/0138000 A1 May 30, 2013

Related U.S. Application Data

(63) Continuation of application No. PCT/JP2011/065966, filed on Jul. 13, 2011.

(30) Foreign Application Priority Data

Jul. 28, 2010 (JP) ................................. 2010-169171

(51) Int. Cl.
*A61B 5/021* (2006.01)
*A61B 5/0225* (2006.01)
(Continued)

(52) U.S. Cl.
CPC ........ *A61B 5/02141* (2013.01); *A61B 5/0225* (2013.01); *A61B 5/02225* (2013.01); *A61B 5/02233* (2013.01); *A61B 17/132* (2013.01)

(58) Field of Classification Search
CPC ............ A61B 5/02141; A61B 5/02225; A61B 5/0225; A61B 5/021; A61B 5/022;
(Continued)

(56) References Cited

U.S. PATENT DOCUMENTS

| 2009/0163823 | A1 | 6/2009 | Takahashi et al. |
| 2009/0312651 | A1* | 12/2009 | Sano ................ A61B 5/02141 600/493 |
| 2010/0324430 | A1* | 12/2010 | Inoue ................ A61B 5/02116 600/493 |

FOREIGN PATENT DOCUMENTS

| JP | 62-268532 A | 11/1987 |
| JP | 03-031404 U | 3/1991 |

(Continued)

OTHER PUBLICATIONS

Office Action issued in corresponding Japanese Application No. 2010-169171 dated Jul. 1, 2014, and English translation thereof (6 pages).

(Continued)

*Primary Examiner* — Michael Kahelin
*Assistant Examiner* — Tho Tran
(74) *Attorney, Agent, or Firm* — Osha Liang LLP

(57) ABSTRACT

A blood pressure measurement device includes a measurement air bladder for being wrapped around a body part to be measured, a compression member that compresses the measurement air bladder from the outside of the measurement air bladder against the body part to be measured; an inflation member for inflating the measurement air bladder, a deflation member for deflating the measurement air bladder, a blood pressure determination unit that determines a blood pressure during the inflation by the inflation member or during the deflation by the deflation member, and a control unit that causes the compression member to apply a pressure that is higher than or equal to an atmospheric pressure to the measurement air bladder when an internal pressure of the measurement air bladder reaches or falls below a certain pressure due to the deflation by the deflation member.

5 Claims, 10 Drawing Sheets

(51) Int. Cl.
*A61B 17/132* (2006.01)
*A61B 5/022* (2006.01)

(58) Field of Classification Search
CPC .............. A61B 5/0235; A61B 606/203; A61B 606/204; A61B 17/135; A61B 17/132; A61B 5/02233; A61H 39/04
See application file for complete search history.

(56) References Cited

FOREIGN PATENT DOCUMENTS

| | | |
|---|---|---|
| JP | 06-014889 A | 1/1994 |
| JP | 2005-305028 A | 11/2005 |
| JP | 3117969 U | 1/2006 |
| JP | 2010-075562 A | 4/2010 |
| WO | 2007/066461 A1 | 6/2007 |

OTHER PUBLICATIONS

Patent Abstracts of Japan, Publication No. 2005-305028, Published on Nov. 4, 2005, 1 page.
Patent Abstracts of Japan, Publication No. 06-014889, Published on Jan. 25, 1994, 1 page.
Patent Abstracts of Japan, Publication No. 2010-075562, Published on Apr. 8, 2010, 1 page.
International Search Report issued in corresponding International Application No. PCT/JP2011/065966 dated Aug. 16, 2011, and English translation thereof (4 pages).

* cited by examiner

BLOOD PRESSURE MEASUREMENT DEVICE

TECHNICAL FIELD

The present invention relates to a blood pressure measurement device, and more specifically to a blood pressure measurement device that compresses a body part to be measured with a measurement air bladder automatically wrapped around the body part to be measured when measuring blood pressure.

BACKGROUND ART

In order to wrap a measurement air bladder around a body part to be measured at an appropriate strength, conventional blood pressure measurement devices preliminarily inflate the measurement air bladder at the start of measurement of blood pressure.

The measurement air bladder is embedded in a measurement cuff together with, for example, a compression air bladder, which is one example of a means to compress the measurement air bladder. Blood pressure is measured based on changes in the pressure of the measurement air bladder.

The aforementioned preliminary inflation is disclosed in, for example, Patent Literature 1 (JP 2005-305028A). According to Patent Literature 1, after a predetermined amount of air is supplied to a measurement air bladder, the rate of increase in the pressure of a compression air bladder is detected while increasing the pressure of the compression air bladder. Following the start of the pressure increase, a process of wrapping the measurement air bladder is completed when a predetermined rate of increase in the pressure is detected.

Measurement of blood pressure based on changes in the pressure of a measurement air bladder is disclosed in, for example, Patent Literature 2 (JP S62-268532A). More specifically, pressure pulse waves (changes in the internal pressure of the measurement air bladder) with amplitudes corresponding to thresholds (Th_SBP and Th_DBP) with respect to the maximum pressure pulse wave value are calculated as pressure values. Note that these thresholds are detected using the following Expressions 1 and 2. Note that in the following Expressions 1 and 2, $Amp_{Max}$ is the maximum pressure pulse wave amplitude value, and $\alpha_{SBP}$, $\beta_{SBP}$, $\alpha_{DBP}$ and $\beta_{DBP}$ are constants that are obtained experimentally.

$$Th\_SBP = Amp_{Max} \times \alpha_{SBP} + \beta_{SBP} \quad \text{(Expression 1)}$$

$$Th\_DBP = Amp_{Max} \times \alpha_{DBP} + \beta_{DBP} \quad \text{(Expression 2)}$$

Patent Literature 1: JP 2005-305028A
Patent Literature 2: JP S62-268532A

SUMMARY OF INVENTION

According to the technology described in Patent Literature 1, the air is evacuated from the measurement air bladder at the end of measurement. When this evacuation cannot be performed in a satisfactory manner for some reason, the amount of air left in the measurement air bladder at the start of measurement may vary. During the aforementioned preliminary inflation, supply of the air to the measurement air bladder is controlled based on a time period of driving of an inflation mechanism. Hence, when the amount of air left in the measurement air bladder at the start of measurement varies, the amount of air supplied to the measurement air bladder during the aforementioned preliminary inflation varies. This could result in variations in the wrapping strength of a cuff after the preliminary inflation.

Variations in the wrapping strength of the cuff at the start of measurement may lead to variations in the calculated blood pressure values. The aforementioned pressure pulse waves used in the calculation of blood pressure are detected under the assumption that a change in the capacity of the measurement air bladder caused by a volumetric change in an artery during pressurization or depressurization of a body part to be measured is a change in the pressure. Variations in the amount of air in the measurement air bladder during the preliminary inflation and variations in the wrapping strength cause the amount of air in the measurement air bladder to change. As a result, the magnitude of the detected pressure pulse waves changes, and the blood pressure values vary as can be understood from the above Expressions 1 and 2.

Therefore, one or more embodiments of the present invention suppress variations in the wrapping strength of a cuff of a blood pressure measurement device at the start of measurement.

A blood pressure measurement device according to one or more embodiments of the present invention includes: a measurement air bladder for being wrapped around a body part to be measured; a compression member that compresses the measurement air bladder from the outside of the measurement air bladder against the body part to be measured; an inflation member for inflating the measurement air bladder; a deflation member for deflating the measurement air bladder; a blood pressure determination unit that determines a blood pressure during the inflation by the inflation member or during the deflation by the deflation member; and a control unit that causes the compression member to apply a pressure that is higher than or equal to an atmospheric pressure to the measurement air bladder when an internal pressure of the measurement air bladder reaches or falls below a certain pressure due to the deflation by the deflation member. In the blood pressure measurement device, the compression member includes a compression air bladder positioned outside the measurement air bladder, and the control unit causes the compression air bladder to apply a pressure that is higher than or equal to the atmospheric pressure to the measurement air bladder by controlling an internal pressure of the compression air bladder.

One or more embodiments of the present invention can suppress variations in the wrapping strength of a cuff at the start of measurement.

DETAILED DESCRIPTION OF INVENTION

Figure 1:
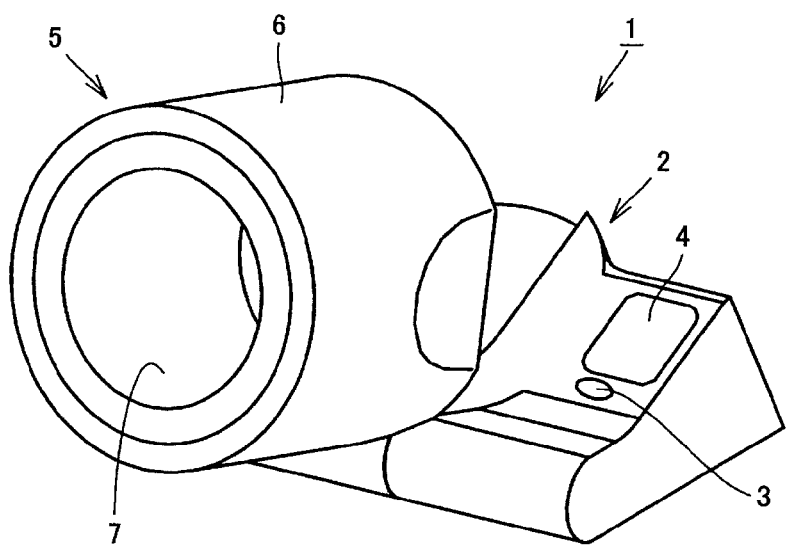
FIG. 1 is a perspective view showing a specific example of an external appearance of a blood pressure measurement device (sphygmomanometer) according to one embodiment of the present invention.

The following describes an embodiment of the present invention with reference to the drawings. Throughout the following description, the same components and constituent elements are given the same reference numeral. Such components and constituent elements with the same reference numeral have the same name and functions.

1. Overall Configuration

FIG. 1 is a perspective view showing a specific example of an external appearance of a blood pressure measurement device (hereinafter referred to as a sphygmomanometer) 1 according to one embodiment of the present invention.

Referring to FIG. 1, the sphygmomanometer 1 according to the present embodiment mainly includes a main body 2 that is placed on, for example, a desk and a measurement member 5 into which an upper arm of a person subjected to the measurement, namely a body part to be measured, is inserted. An operation unit 3, a display unit 4 and an elbow rest are arranged on the upper portion of the main body 2. The operation unit 3 includes, for example, a power switch and a measurement switch. The measurement member 5 is attached to the main body 2 in such a manner that the inclination thereof can be changed. The measurement member 5 includes a housing 6, which is a machine casing having a substantially cylindrical shape, and a live body compression/fixation device placed on the inner circumferential portion of the housing 6. As shown in FIG. 1, under normal usage conditions, the live body compression/fixation device placed on the inner circumferential portion of the housing 6 is covered by a cover 7 and is therefore not exposed.

The display unit 4 can be realized by a known display device such as a liquid crystal display.

Figure 2:
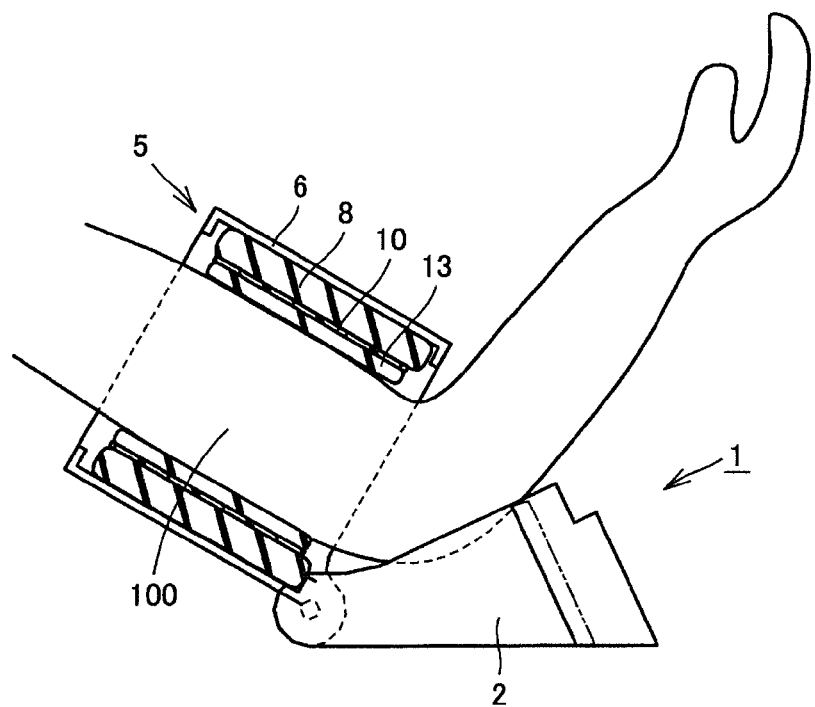
FIG. 2 is a schematic cross-sectional diagram of the sphygmomanometer shown in FIG. 1 at the time of measurement of blood pressure.

FIG. 2 is a schematic cross-sectional diagram of the sphygmomanometer 1 at the time of measurement of blood pressure. As shown in FIG. 2, at the time of measurement of blood pressure, an upper arm 100 is inserted into the housing 6 and the elbow is placed on the aforementioned elbow rest. In this state, an instruction for starting the measurement is issued. Blood pressure is measured while the upper arm 100 is compressed and fixed by the aforementioned live body compression/fixation device.

The live body compression/fixation device includes a measurement air bladder 13, a curler 10 and a compression/fixation air bladder 8. The measurement air bladder 13, which is equivalent to a cuff, compresses a body part to be measured so as to measure blood pressure. The curler 10, which is positioned outside the measurement air bladder 13, is a flexible member that has a substantially cylindrical shape and can expand and contract in a radial direction. The compression/fixation air bladder 8 is a measurement air bladder compression member that is positioned outside the curler 10, causes the curler 10 to radially contract by pressing the outer circumferential surface of the curler 10 toward the inside through inflation, and presses the measurement air bladder 13 against a body part of a live body to be measured via the housing and the curler 10.

2. Internal Configuration of Measurement Member

Figure 3:
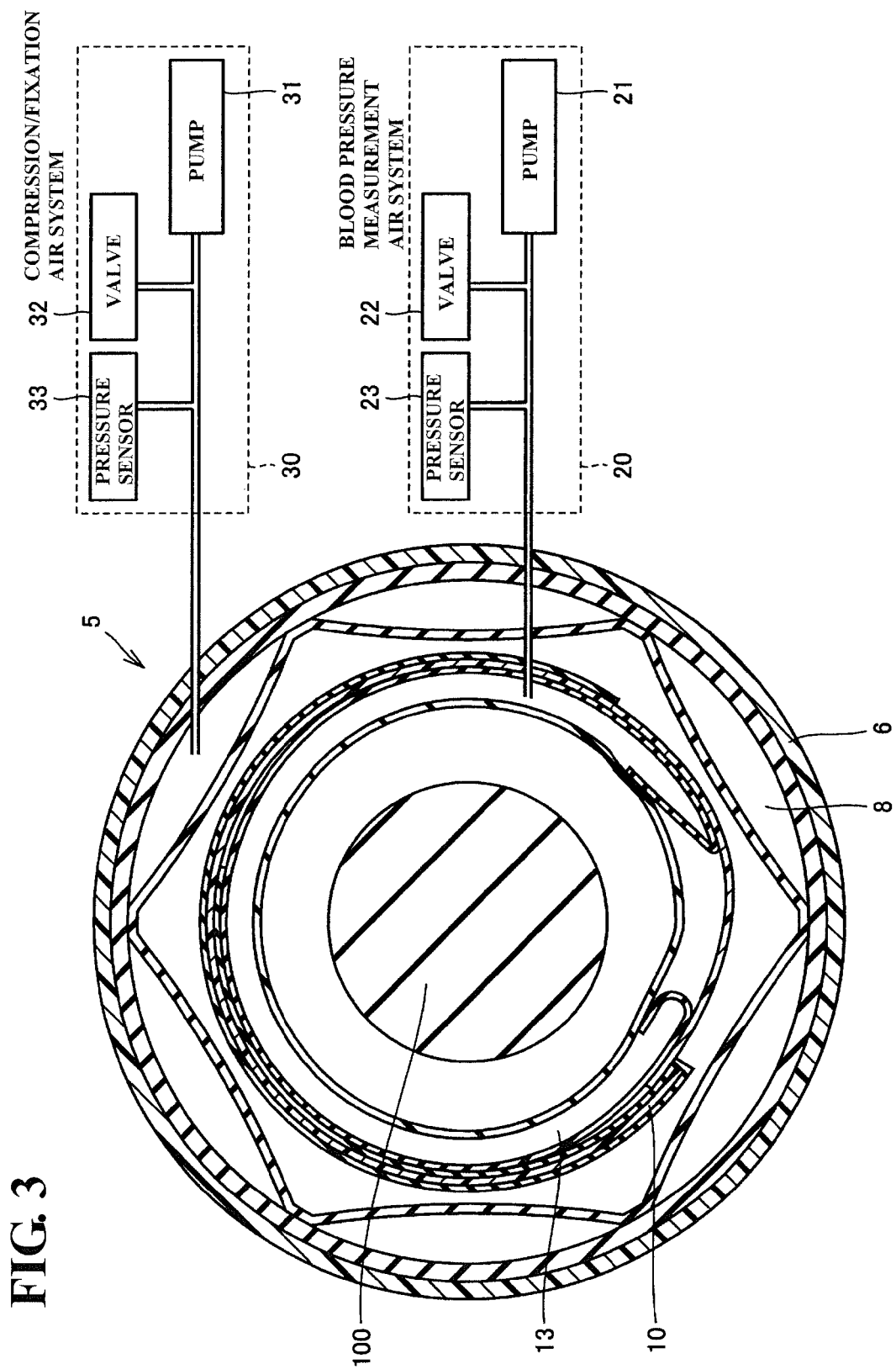
FIG. 3 is a cross-sectional diagram for explaining an internal configuration of a measurement member of the sphygmomanometer shown in FIG. 1.

FIG. 3 is a cross-sectional diagram for explaining an internal configuration of the measurement member 5. As shown in FIG. 3, in the measurement member 5, the compression/fixation air bladder 8 is arranged inside the housing 6. A compression/fixation air system 30 (see FIG. 4), which will be described later, inflates and deflates the compression/fixation air bladder 8.

The curler 10, which is a plate-like member rolled in a substantially cylindrical shape, is arranged inside the compression/fixation air bladder 8. The curler 10 is a thin plate made of flexible material such as plastic, and elastically deforms in a radial direction when an external force is applied thereto.

The measurement air bladder 13 is arranged inside the curler 10. A measurement air system 20 (see FIG. 4), which will be described later, inflates and deflates the measurement air bladder 13.

The curler 10 is wrapped around the measurement air bladder 13 in such a manner that a portion of the curler 10 overlaps another portion of the curler 10 in a wrapping direction.

3. Block COnfiguration

Figure 4:
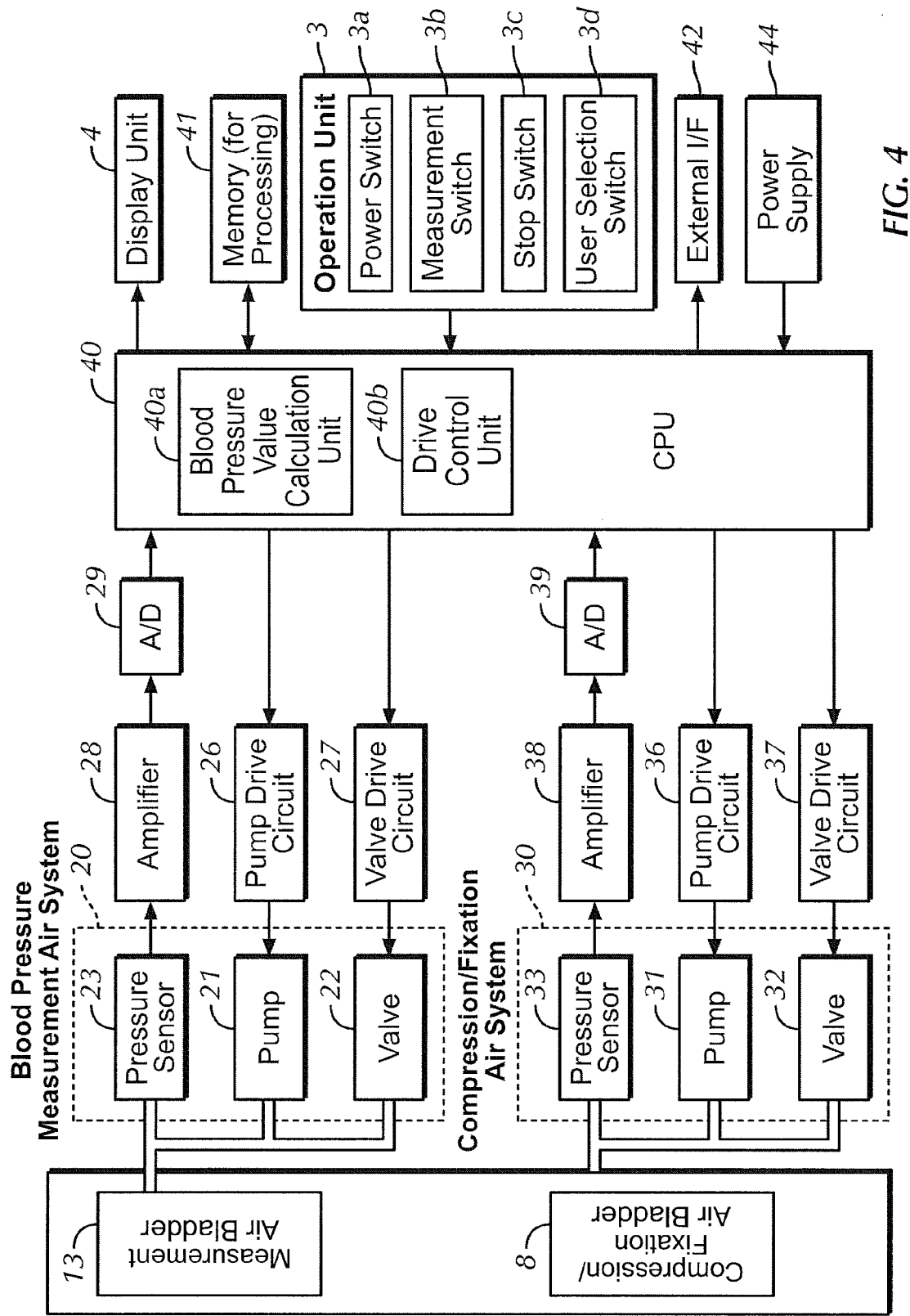
FIG. 4 is a block diagram showing a specific example of a functional configuration of the sphygmomanometer shown in FIG. 1.

FIG. 4 is a block diagram showing a specific example of a functional configuration of the sphygmomanometer 1.

Referring to FIG. 4, the sphygmomanometer 1 includes, in addition to the measurement air bladder 13 and the compression/fixation air bladder 8 described above, the measurement air system 20 and the compression/fixation air system 30 that are connected to the measurement air bladder 13 and the compression/fixation air bladder 8, respectively.

The measurement air system 20 includes a pressure sensor 23 that measures the internal pressure of the measurement air bladder 13, a pump 21 that supplies the air to and evacuates the air from the measurement air bladder 13, and a valve 22. The compression/fixation air system 30 includes a pressure sensor 33 that measures the internal pressure of the compression/fixation air bladder 8, a pump 31 that supplies the air to and evacuates the air from the compression/fixation air bladder 8, and a valve 32.

The sphygmomanometer 1 also includes a central processing unit (CPU) 40, an amplifier 28, a pump drive circuit 26, a valve drive circuit 27, an amplifier 38, a pump drive circuit 36, a valve drive circuit 37, analog to digital (A/D) converters 29 and 39, a memory 41, the display unit 4, the operation unit 3, and a power supply 44. The CPU 40 controls the entirety of the sphygmomanometer 1. The amplifier 28, the pump drive circuit 26 and the valve drive circuit 27 are connected to the measurement air system 20. The amplifier 38, the pump drive circuit 36 and the valve drive circuit 37 are connected to the compression/fixation air bladder 8. The A/D converters 29 and 39 are connected to the amplifiers 28 and 38, respectively. The memory 41 stores programs executed by the CPU 40 and results of measurement. The display unit 4 displays results of measurement and the like. The operation unit 3 includes the measurement switch, the power switch, and the like. The power supply 44 supplies power supplied from an external power supply to the components of the sphygmomanometer 1. Note that the power supply 44 may be a rechargeable battery or a similar element that supplies power to the components of the sphygmomanometer 1 without receiving power from an external power supply.

The CPU 40 includes a drive control unit 40B that executes a predetermined program stored in the memory 41 in accordance with an operation signal input from the operation unit 3, and outputs control signals to the pump drive circuits 26 and 36 and the valve drive circuits 27 and 37. The pump drive circuits 26 and 36 and the valve drive circuits 27 and 37 cause a blood pressure measurement operation to be executed by driving the pumps 21 and 31 and the valves 22 and 32 in accordance with the control signals.

The pressure sensor 23 detects the internal pressure of the measurement air bladder 13 and inputs a detection signal to the amplifier 28. The pressure sensor 33, which is equivalent to a compression degree detection member, detects the internal pressure of the compression/fixation air bladder 8 and outputs a detection signal to the amplifier 38. The internal pressure of the compression/fixation air bladder 8 is equivalent to a degree at which the measurement air bladder is compressed by the measurement air bladder compression member. The input detection signals are amplified to a predetermined amplitude by the amplifiers 28 and 38, converted to digital signals by the A/D converters 29 and 39, and input to the CPU 40.

The CPU 40 executes predetermined processing based on the internal pressures of the measurement air bladder 13 and the compression/fixation air bladder 8 obtained from the pressure sensors 23 and 33, and outputs the aforementioned control signals to the pump drive circuits 26 and 36 and the valve drive circuits 27 and 37 in accordance with the result of the predetermined processing.

The CPU 40 also includes a blood pressure value calculation unit 40A that calculates blood pressure values (a systolic blood pressure value, a diastolic blood pressure value, and/or an average blood pressure value) based on the internal pressure of the measurement air bladder 13 obtained from the pressure sensor 23. The CPU 40 outputs the blood pressure values calculated by the blood pressure value calculation unit 40A to the display unit 4 so as to cause the display unit 4 to display them as a result of measurement.

The operation unit 3 includes a power switch 3A, a measurement switch 3B, a stop switch 3C and a user selection switch 3D. The power switch 3A switches between on and off of power supply to the sphygmomanometer 1. The measurement switch 3B is operated to cause the sphygmomanometer 1 to start measurement of blood pressure. The stop switch 3C is operated to forcibly stop the ongoing measurement. The user selection switch 3D is operated to select a user of the sphygmomanometer 1. When each switch of the operation unit 3 is operated, the CPU 40 performs control corresponding to that switch.

4. Blood Pressure Measurement Processing

Figure 5:
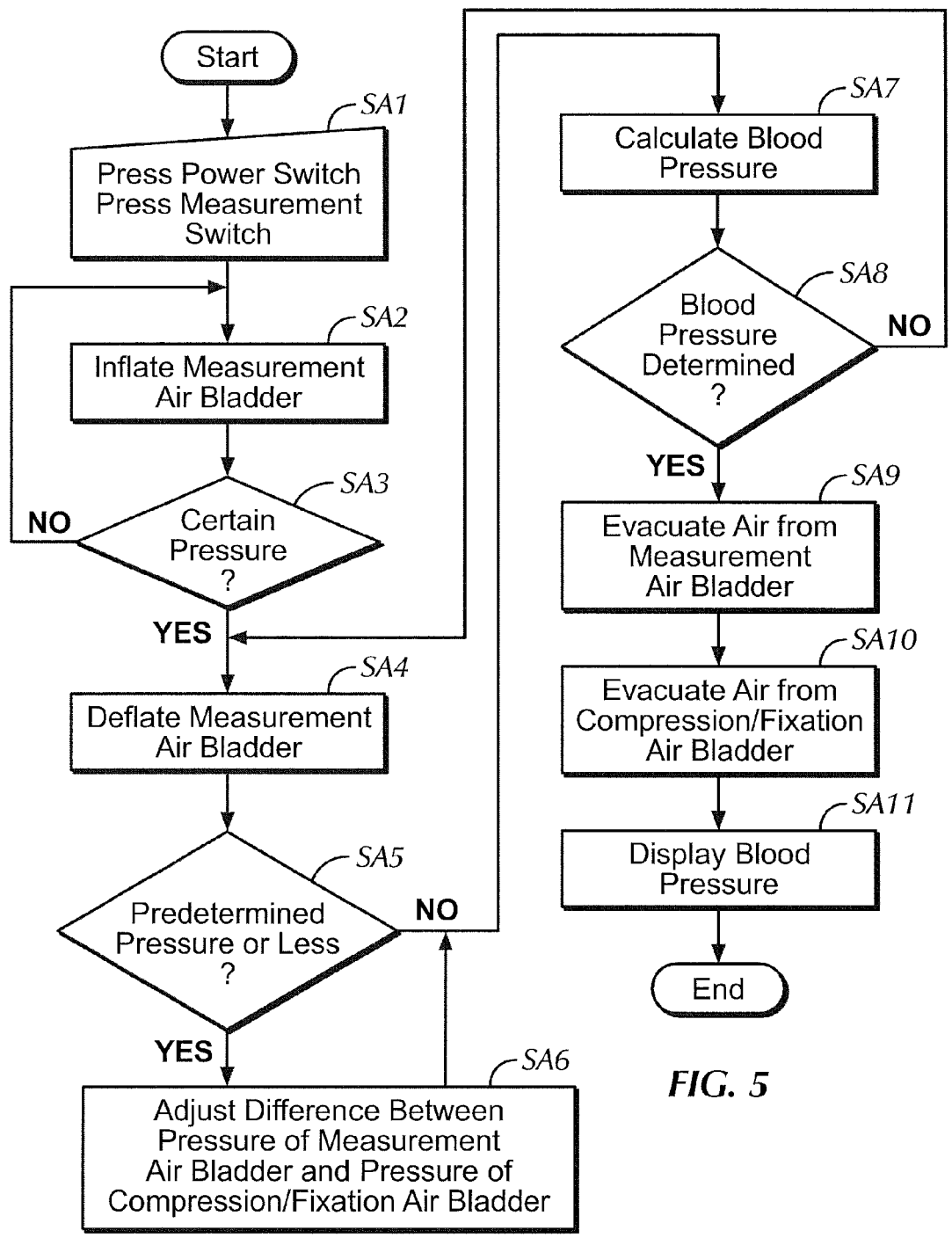
FIG. 5 is a flowchart of blood pressure measurement processing executed by the sphygmomanometer shown in FIG. 1.

FIG. 5 is a flowchart of processing executed by the sphygmomanometer 1 when measuring the blood pressure of a person subjected to the measurement (blood pressure measurement processing).

Referring to FIG. 5, when the power switch 3A is operated, the CPU 40 resets the sphygmomanometer 1 in step SA1.

When the measurement switch 3B is also operated (step SA1), the CPU 40 executes processing for wrapping the cuff around a body part to be measured. For example, in this processing, the CPU 40 supplies a predetermined amount of air to the measurement air bladder 13 and increases the pressure of the compression/fixation air bladder 8. The rate of increase in the pressure of the compression/fixation air bladder 8 is detected. Following the start of the pressure increase, the increase in the pressure of the compression/fixation air bladder 8 is stopped when a predetermined rate of increase in the pressure is detected. As a result, the cuff is wrapped around the body part to be measured.

Next, in step SA2, the inflation of the measurement air bladder 13 is started. Then, the processing moves to step SA3.

In step SA3, the CPU 40 determines whether or not the internal pressure of the measurement air bladder 13 has reached a certain pressure. When the CPU 40 determines that the internal pressure of the measurement air bladder 13 has reached the certain pressure, the processing moves to step SA4. Note that the certain pressure is sufficiently higher than the systolic blood pressure of a person subjected to measurement (approximately by 20 mmHg to 30 mmHg). For example, the certain pressure may be a value stored in the memory 41 in advance, may be calculated based on a systolic blood pressure value detected in a simple way during the increase in the internal pressure of the measurement air bladder 13, or may be calculated based on the past results of measurement of systolic blood pressure values stored in the memory 41 for a person currently subjected to measurement. The CPU 40 can read blood pressure values measured in the past for a person currently subjected to measurement by storing the past results of measurement of blood pressure values in the memory 41 for each person subjected to measurement and receiving, as the input, information for identifying a person subjected to measurement in step SA1.

In step SA4, the CPU 40 starts the deflation of the measurement air bladder 13. Then, the processing moves to step SA5. The measurement air bladder 13 can be deflated by opening the valve 22. Alternatively, the measurement air bladder 13 may be deflated by driving a pump that is separately provided to deflate the measurement air bladder 13.

Figure 6:
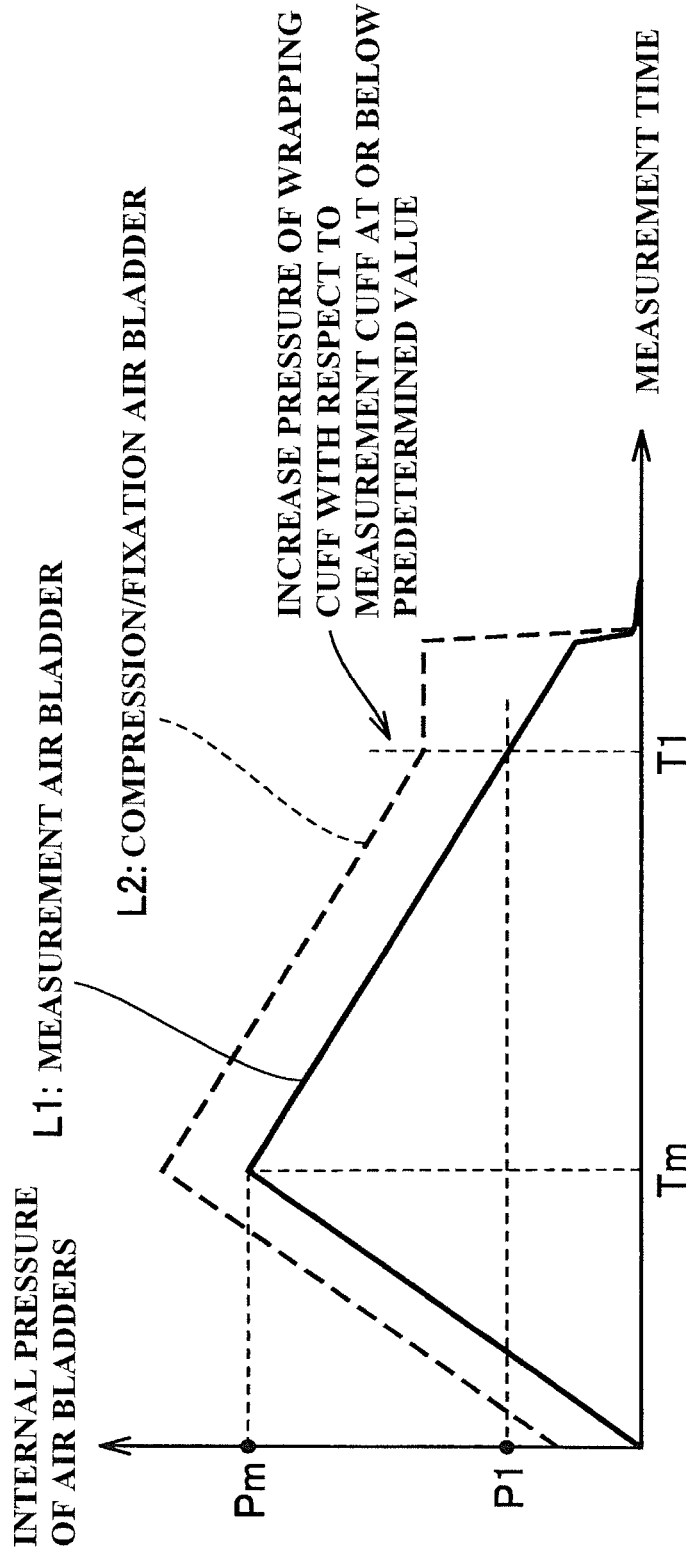
FIG. 6 shows an example of changes in the internal pressures of a measurement air bladder and a compression/fixation air bladder in the blood pressure measurement processing shown in FIG. 5.

When decreasing the internal pressure of the measurement air bladder 13, the CPU 40 adjusts the internal pressure of the compression/fixation air bladder 8 to maintain a certain relationship with the internal pressure of the measurement air bladder 13. More specifically, the CPU 40 adjusts the internal pressure of the compression/fixation air bladder 8 to be higher than the internal pressure of the measurement air bladder 13 and to have a certain pressure difference from the internal pressure of the measurement air bladder 13. FIG. 6 shows an example of changes in the internal pressures of the measurement air bladder 13 and the compression/fixation air bladder 8.

In FIG. 6, the horizontal axis represents the measurement time, and the vertical axis represents the internal pressure of the measurement air bladder 13 and the compression/fixation air bladder 8. Also, in FIG. 6, the internal pressure of the measurement air bladder 13 is shown by a solid line (L1) and the internal pressure of the compression/fixation air bladder 8 is shown by a dashed line (L2).

Following the start of measurement, the measurement air bladder 13 is inflated. When the internal pressure of the measurement air bladder 13 reaches a certain pressure (pressure Pm in FIG. 6), the measurement air bladder 13 is deflated. Once the deflation of the measurement air bladder 13 has been started, the internal pressure of the compression/fixation air bladder 8 is controlled so that a difference between the internal pressure of the compression/fixation air bladder 8 and the internal pressure of the measurement air bladder 13 has a certain value. This control can be realized by, for example, adjusting the degree at which the valve 32 is opened based on a detected value of the internal pressure of the measurement air bladder 13. This control maintains a difference between the internal pressure of the compression/fixation air bladder 8 and the internal pressure of the measurement air bladder 13 at a certain value from the measurement time Tm, i.e. when the internal pressure of the measurement air bladder 13 reached Pm, to the measurement time T1.

Then, the CPU 40 extracts oscillation components associated with volumetric changes in an artery superimposed on the internal pressure of the measurement air bladder 13 during the deflation of the measurement air bladder 13, and calculates blood pressure values using known calculation processing (step SA7).

In step SA5, the CPU 40 determines whether or not the internal pressure of the measurement air bladder 13 has reached a predetermined pressure (P1) in parallel with the aforementioned calculation of blood pressure values. When the CPU 40 determines that the internal pressure of the measurement air bladder 13 has reached the predetermined pressure, the processing moves to step SA6.

In step SA6, the internal pressure of the compression/fixation air bladder 8 is adjusted so that a difference between the internal pressure of the measurement air bladder 13 and the internal pressure of the compression/fixation air bladder 8 is greater than or equal to a certain value. This adjustment of the internal pressure of the compression/fixation air bladder 8 can be realized through control for suppressing the evacuation of the air from the compression/fixation air bladder 8 by closing the valve 32 or by decreasing the degree at which the valve 32 is opened. As shown in FIG. 6, this control makes a difference between the internal pressure of the measurement air bladder 13 and the internal pressure of the compression/fixation air bladder 8 greater after the measurement time T1, i.e. when the internal pressure of the measurement air bladder 13 dropped to P1, than during a time period from Tm to T1.

Due to this internal pressure difference, the compression/fixation air bladder 8 can apply pressure that is higher than or equal to the atmospheric pressure to the measurement air bladder 13. That is to say, this internal pressure difference enables the compression/fixation air bladder 8 to overcome the frictional force of the overlapping portions of the curler 10 and apply pressure that is higher than or equal to the atmospheric pressure to the measurement air bladder 13.

When the CPU 40 determines that the measurement of blood pressure is completed (the YES branch of step SA8) while the measurement of blood pressure (step SA7) is executed in parallel with the adjustment of the internal pressure of the compression/fixation air bladder 8 (step SA6), the processing moves to step SA9.

In step SA9, in order to complete the evacuation of the air from the measurement air bladder 13, the CPU 40 leaves the valve 22 open for a predetermined time period or longer while maintaining the aforementioned state where the difference between the internal pressure of the measurement air bladder 13 and the internal pressure of the compression/fixation air bladder 8 is greater than or equal to the certain value. Thereafter, the processing moves to step SA10.

In step SA10, the CPU 40 evacuates the air from the compression/fixation air bladder 8 (maintains the state where the valve 32 is left open for a certain time period or longer). Thereafter, the processing moves to step SA11.

In step SA11, the CPU 40 causes the display unit 4 to display the measured blood pressure values and completes the blood pressure measurement processing.

According to the above-described blood pressure measurement processing, after the measurement of blood pressure is completed, the state where a difference between the internal pressure of the measurement air bladder 13 and the internal pressure of the compression/fixation air bladder 8 is greater than or equal to a certain value is maintained for a certain time period or longer. This facilitates the evacuation of the air from the measurement air bladder 13. As a result, the air is reliably evacuated from the measurement air bladder 13 upon completion of the measurement of blood pressure.

5. Modification Example (1)

According to the above-described blood pressure measurement processing, once the internal pressure of the measurement air bladder 13 drops to P1, the internal pressure of the compression/fixation air bladder 8 is controlled such that the aforementioned internal pressure difference is greater than or equal to a certain value.

Note that the above-described blood pressure measurement processing detects the internal pressure of the measurement air bladder 13 and, on the condition that the detected value has reached P1, starts controlling the internal pressure of the compression/fixation air bladder 8 such that the aforementioned internal pressure difference is greater than or equal to the certain value. For example, the above-described blood pressure measurement processing may estimate, in advance, a time period that elapses from when the measurement is started or the deflation of the measurement air bladder 13 (step SA4) is started to when the internal pressure of the measurement air bladder 13 reaches or falls below P1. In this case, on the condition that this time period has elapsed, the above-described blood pressure measurement processing may start controlling the internal pressure of the compression/fixation air bladder 8 such that the aforementioned internal pressure difference is greater than or equal to the certain value.

This time period can be estimated based on, for example, blood pressure values measured in the past for a person currently subjected to measurement (stored in the memory 41), blood pressure values (a diastolic blood pressure value, an average blood pressure value, and/or a systolic blood pressure value) tentatively detected in the inflation process (step SA2) for a person subjected to measurement, and the speed of the deflation of the measurement air bladder 13 (step SA4).

6. Modification Example (2)

In the above embodiment, the curler 10 is arranged between the measurement air bladder 13 and the compression/fixation air bladder 8. Although the curler 10 is arranged for the purpose of, for example, uniformly spreading the measurement air bladder 13 in the circumferential direction of a body part to be measured, there are cases where the curler 10 is not an essential constituent element of the sphygmomanometer 1.

Figure 7:
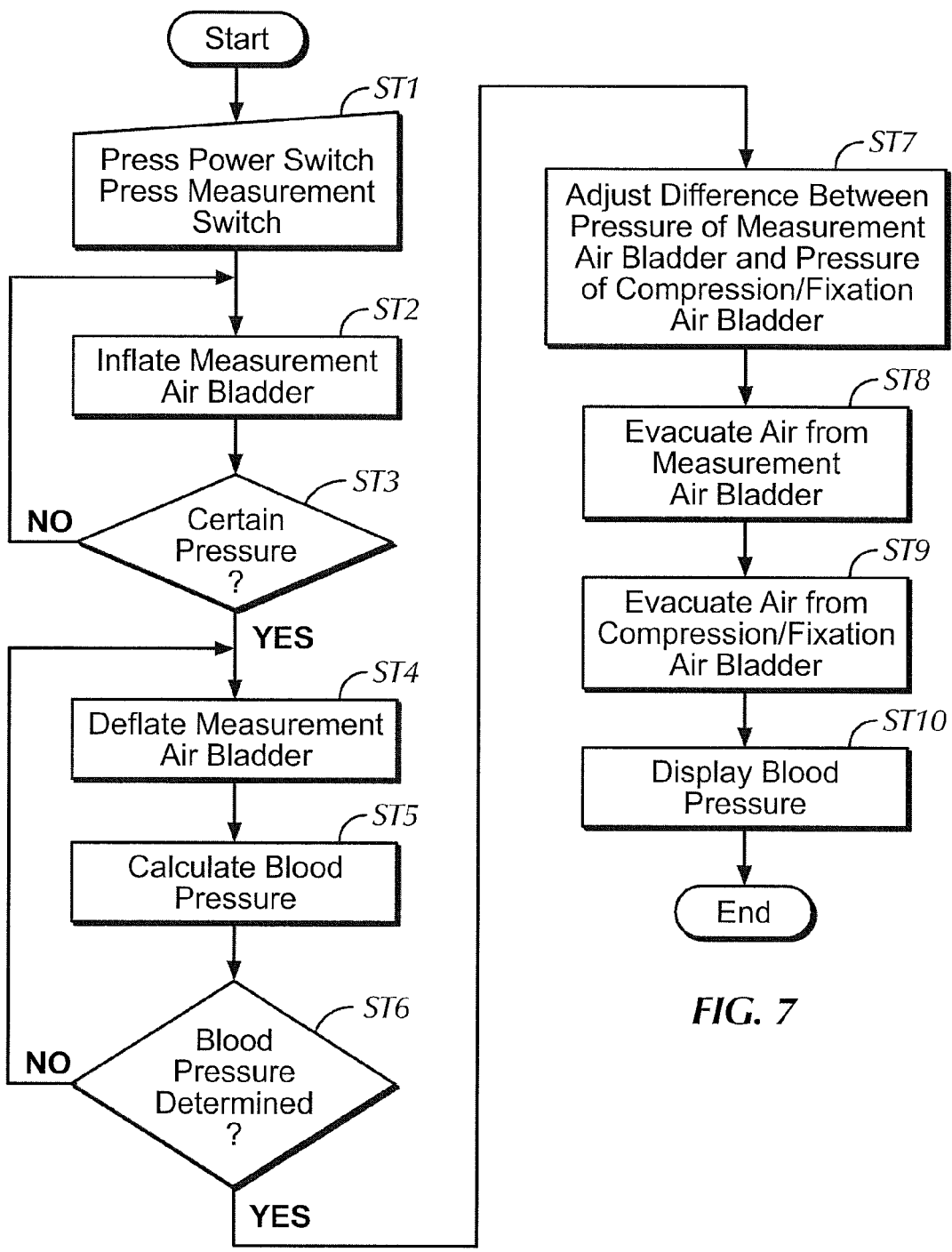
FIG. 7 is a flowchart of blood pressure measurement processing executed by the sphygmomanometer shown in FIG. 1 according to Modification Example (2).

FIG. 7 is a flowchart of blood pressure measurement processing executed by the sphygmomanometer 1 that is not provided with the curler 10.

Referring to FIG. 7, when the power switch 3A is operated, the CPU 40 resets the sphygmomanometer 1 in step ST1 in a manner similar to step SA1.

When the measurement switch 3B is also operated (step ST1), the CPU 40 executes processing for wrapping the cuff around a body part to be measured in a manner similar to step SA1.

Next, in step ST2, the CPU 40 starts the inflation of the measurement air bladder 13 in a manner similar to step SA2. Then, the processing moves to step ST3.

In step ST3, the CPU 40 determines whether or not the internal pressure of the measurement air bladder 13 has reached a certain pressure in a manner similar to step SA3. When the CPU 40 determines that the internal pressure of the measurement air bladder 13 has reached the certain pressure, the processing moves to step ST4.

In step ST4, the CPU 40 starts the deflation of the measurement air bladder 13 in a manner similar to step SA4. Then, the processing moves to step ST5.

Figure 8:
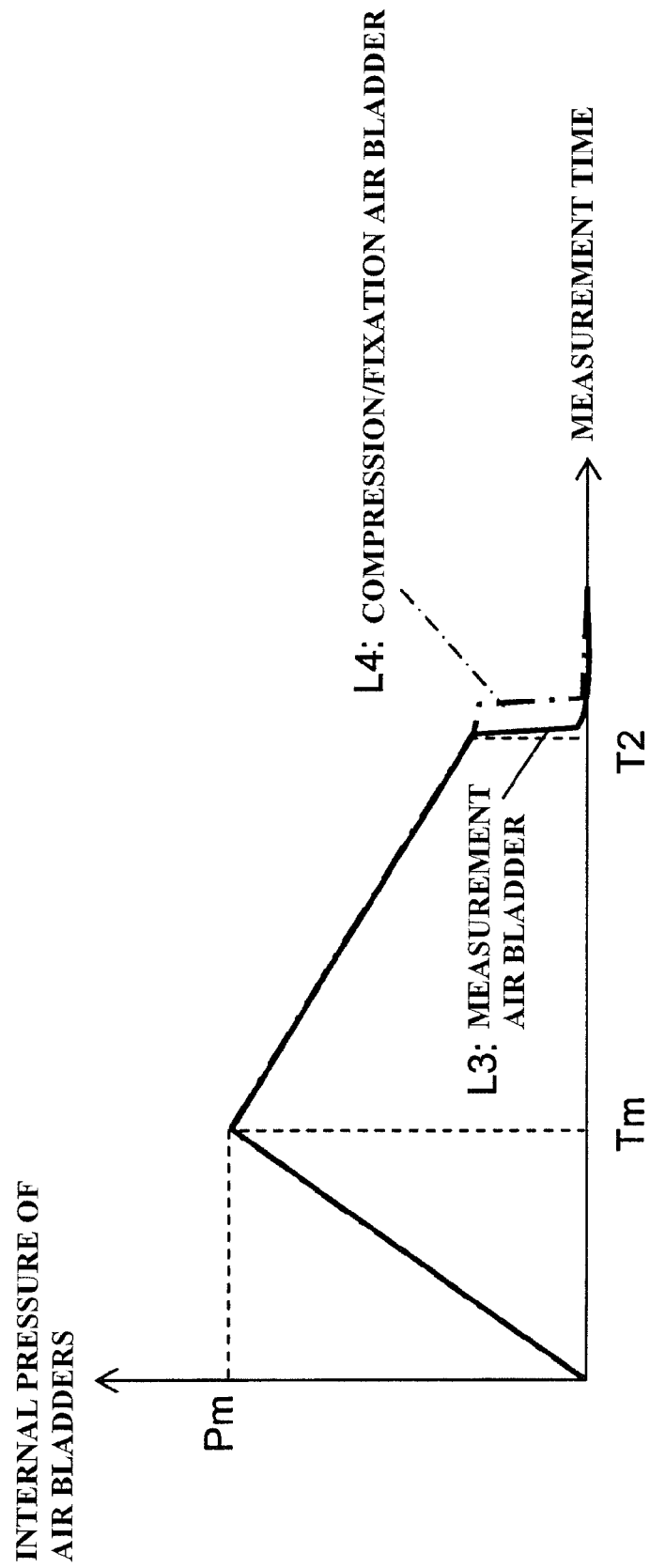
FIG. 8 shows an example of changes in the internal pressures of a measurement air bladder and a compression/fixation air bladder in the blood pressure measurement processing shown in FIG. 7.

When decreasing the internal pressure of the measurement air bladder 13 in step ST4, the CPU 40 adjusts the internal pressure of the compression/fixation air bladder 8 to maintain a certain relationship with the internal pressure of the measurement air bladder 13. More specifically, the CPU 40 adjusts the internal pressure of the compression/fixation air bladder 8 to be equal to the internal pressure of the measurement air bladder 13. FIG. 8 shows an example of changes in the internal pressures of the measurement air bladder 13 and the compression/fixation air bladder 8.

In FIG. 8, the horizontal axis represents the measurement time, and the vertical axis represents the internal pressure of the measurement air bladder 13 and the compression/fixation air bladder 8. Also, in FIG. 8, the internal pressure of the measurement air bladder 13 is shown by a solid line (L3), and the internal pressure of the compression/fixation air bladder 8 is shown by a dashed line (L4).

Following the start of measurement, the measurement air bladder 13 is inflated. When the internal pressure of the measurement air bladder 13 reaches a certain pressure (pressure Pm in FIG. 8), the measurement air bladder 13 is deflated. Once the deflation of the measurement air bladder 13 has been started, the internal pressure of the compression/fixation air bladder 8 is controlled to have the same value as the internal pressure of the measurement air bladder 13. This control can be realized by, for example, adjusting the degree at which the valve 32 is opened based on a detected value of the internal pressure of the measurement air bladder 13. As a result of this control, the internal pressure of the compression/fixation air bladder 8 and the internal pressure of the measurement air bladder 13 are maintained at the same value from the measurement time Tm, i.e. when the internal pressure of the measurement air bladder 13 reached Pm, to the measurement time T2.

Then, the CPU 40 extracts oscillation components associated with volumetric changes in an artery superimposed on the internal pressure of the measurement air bladder 13 during the deflation of the measurement air bladder 13, and calculates blood pressure values using known calculation processing (step ST5).

Thereafter, the CPU 40 determines whether or not calculation of the blood pressure values (a diastolic blood pressure value, an average blood pressure value, and/or a systolic blood pressure) has been completed in step ST6. When the CPU 40 determines that calculation of the blood pressure values has been completed, the processing moves to step ST7.

In step ST7, the internal pressure of the compression/fixation air bladder 8 is adjusted so that a difference between the internal pressure of the measurement air bladder 13 and the internal pressure of the compression/fixation air bladder 8 is greater than or equal to a certain value. This adjustment of the internal pressure of the compression/fixation air bladder 8 can be realized through control for suppressing the evacuation of the air from the compression/fixation air bladder 8 by closing the valve 32 or by decreasing the degree at which the valve 32 is opened. In the present modification example, the valve 22 is opened. As a result of this control, the difference between the internal pressure of the measurement air bladder 13 and the internal pressure of the compression/fixation air bladder 8 is greater than or equal to the aforementioned certain value after the completion of calculation of the blood pressure values (the measurement time T2), as shown in FIG. 8.

Due to this internal pressure difference, the compression/fixation air bladder 8 can apply pressure that is higher than or equal to the atmospheric pressure to the measurement air bladder 13. That is to say, this internal pressure difference enables the compression/fixation air bladder 8 to apply pressure that is higher than or equal to the atmospheric pressure to the measurement air bladder 13.

Consequently, as can be understood from FIG. 8, the amount of decrease in the pressure of the measurement air bladder 13 per unit time is larger after T2 than during a time period from Tm to T2.

In step ST8, the CPU 40 controls the internal pressure of the compression/fixation air bladder 8 so that the difference between the internal pressure of the measurement air bladder 13 and the internal pressure of the compression/fixation air bladder 8 is maintained at or above the aforementioned certain value until a certain time period elapses since the start of the process of step ST7. Thereafter, the processing moves to step ST9. The CPU 40 may proceed to the process of step ST9 on the condition that a certain time period has elapsed since the internal pressure of the measurement air bladder 13 reached or fell below a certain value.

In step ST9, the CPU 40 evacuates the air from the compression/fixation air bladder 8 (maintains the state where the valve 32 is left open for a certain time period or longer). Thereafter, the processing moves to step ST10.

In step ST10, the CPU 40 causes the display unit 4 to display the measured blood pressure values and completes the blood pressure measurement processing.

7. Modification Example (3)

In the above embodiment, the evacuation of the air from the measurement air bladder 13 is facilitated by decreasing the degree at which the valve 32 connected to the compression/fixation air bladder 8 is opened or by closing the valve 32. The evacuation of the air from the measurement air bladder 13 may be facilitated by further inflating the compression/fixation air bladder 8 after the measurement time T1 (FIG. 6) or after the measurement time T2 (FIG. 8).

Alternatively, the evacuation of the air from the measurement air bladder 13 may be facilitated by driving a deflation pump connected to the measurement air bladder 13.

8. Modification Example (4)

In the above embodiment, the evacuation of the air from the measurement air bladder 13 is facilitated by the compression/fixation air bladder 8 compressing the measurement air bladder 13.

Figure 9:
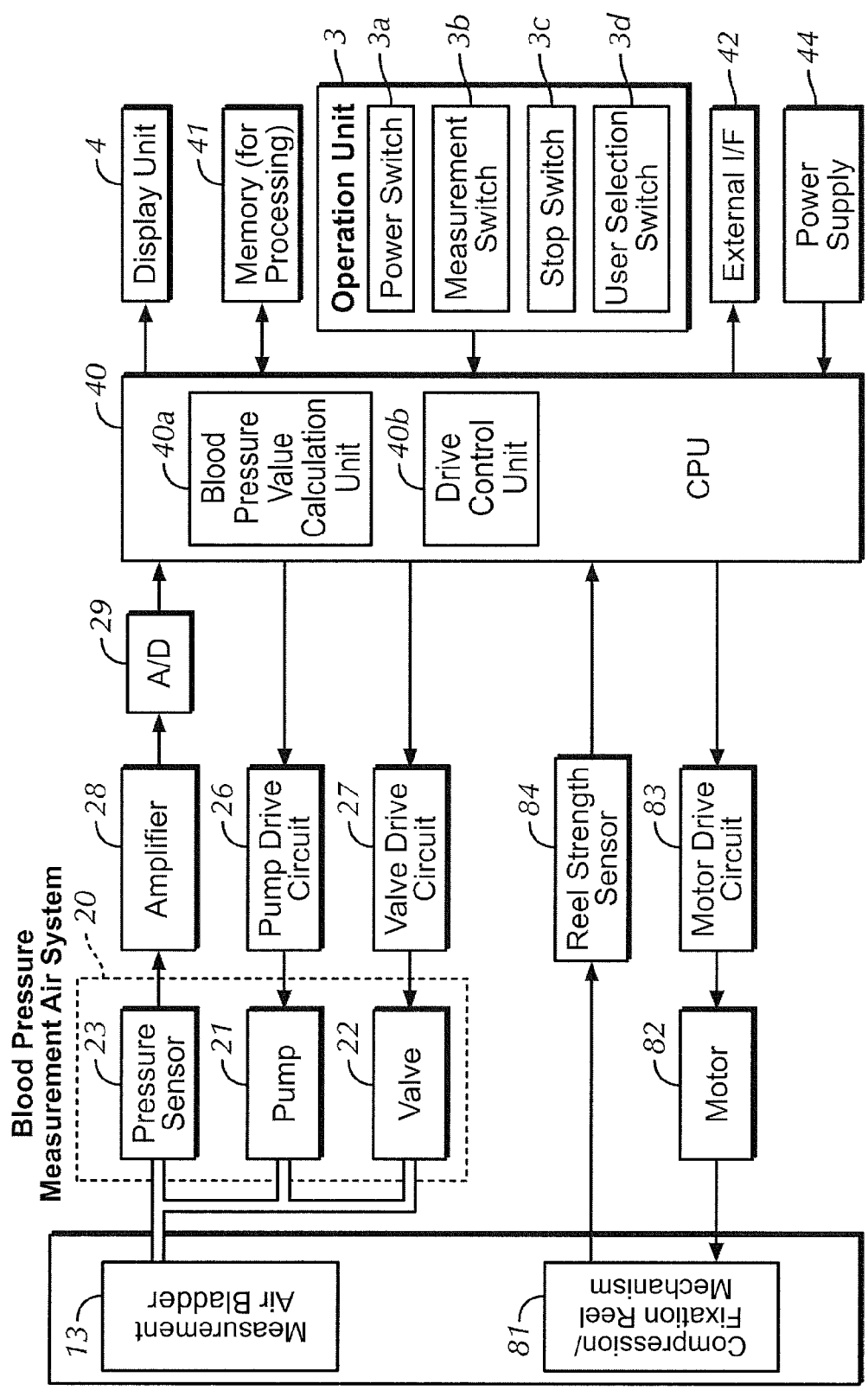
FIG. 9 is a block diagram of the sphygmomanometer shown in FIG. 1 according to Modification Example (4).
Figure 10:
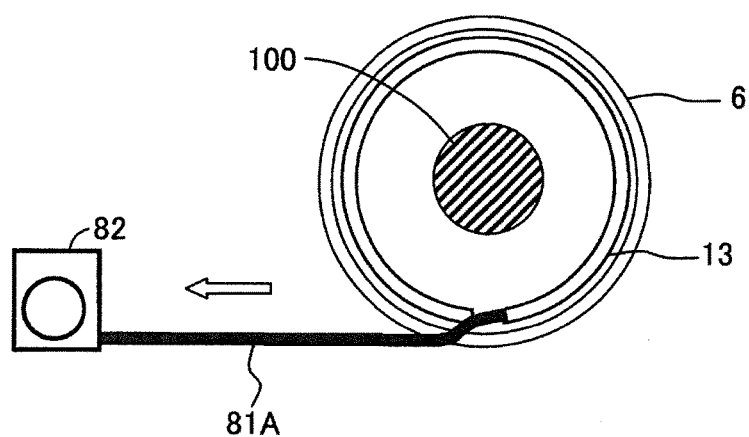
FIG. 10 is a schematic cross-sectional diagram of the sphygmomanometer shown in FIG. 1 according to Modification Example (4) in the vicinity of a body part to be measured.

In the sphygmomanometer 1, the evacuation of the air from the measurement air bladder 13 may be facilitated by a mechanism for tightening the measurement air bladder 13 using a wire and the like so as to press the measurement air bladder 13 against a body part to be measured, instead of the compression/fixation air bladder 8. FIG. 9 is a block diagram of the sphygmomanometer 1 according to this modification example. FIG. 10 shows a schematic cross-section of the vicinity of the body part to be measured in this modification example.

Referring to FIGS. 9 and 10, the sphygmomanometer 1 according to the present modification example includes a compression/fixation reel mechanism 81 provided with the aforementioned wire 81A, instead of the compression/fixation air bladder 8. One end of the compression/fixation reel mechanism 81 is fixed to the measurement air bladder 13. The other end of the compression/fixation reel mechanism 81 is housed in a reel device that includes a motor 82. The forward rotation of the motor 82 causes the compression/fixation reel mechanism 81 to reel the wire 81A in the direction of a white arrow in FIG. 10. As a result, the measurement air bladder 13 is wrapped around the body part to be measured.

The reverse rotation of the motor 82 causes the compression/fixation reel mechanism 81 to release the reeled wire 81A in the direction opposite to the direction of the white arrow in FIG. 10. As a result, wrapping of the measurement air bladder 13 around the body part to be measured by the compression/fixation reel mechanism 81 is released.

The sphygmomanometer 1 according to the present modification example includes a motor drive circuit 83 for driving the motor 82. The motor drive circuit 83 is controlled by the CPU 40.

Figure 11:
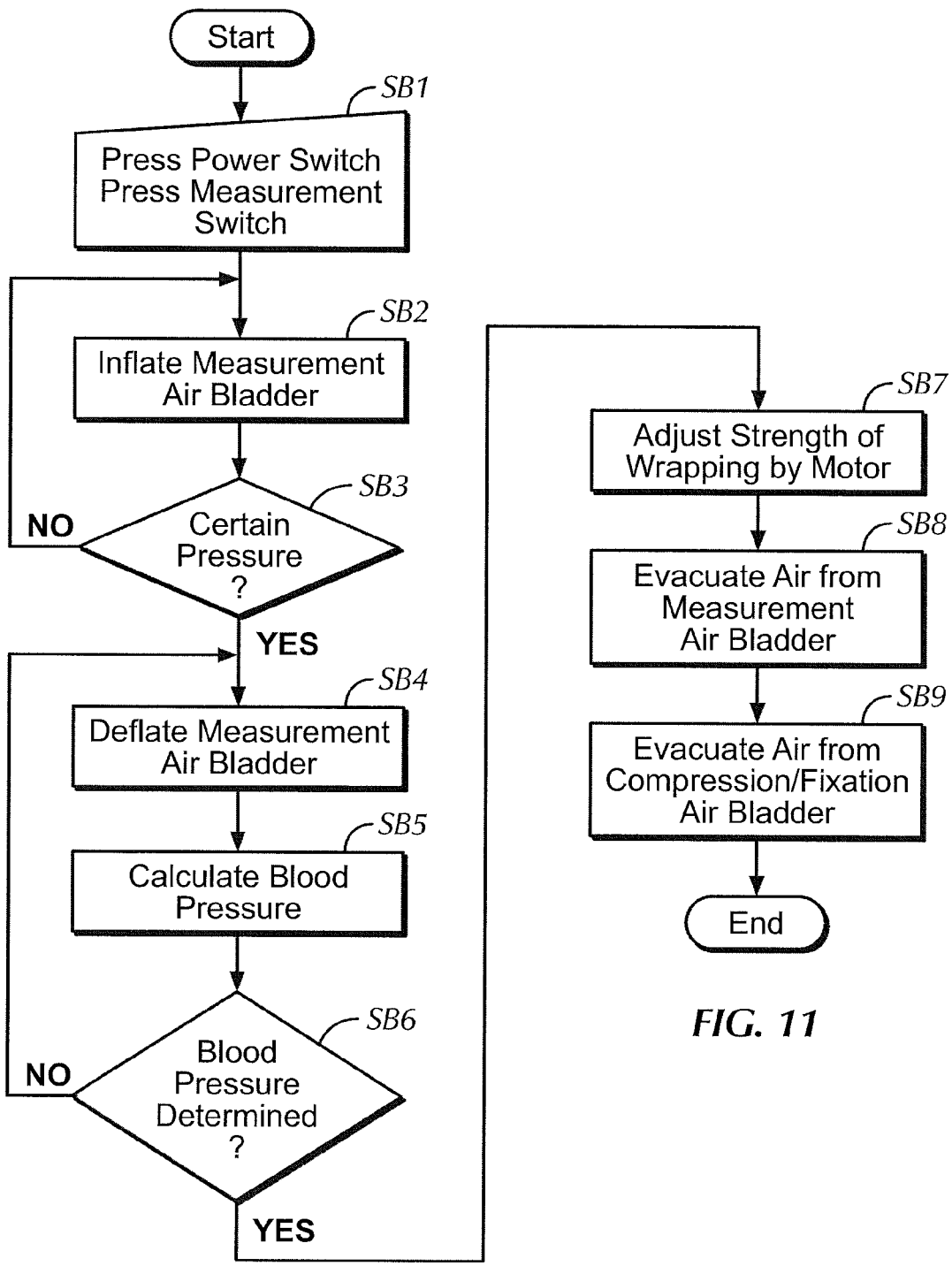
FIG. 11 is a flowchart of blood pressure measurement processing executed by the sphygmomanometer shown in FIG. 9.

FIG. 11 is a flowchart of blood pressure measurement processing executed by the sphygmomanometer 1 according to the present modification example.

Referring to FIG. 11, when the power switch 3A is operated, the CPU 40 resets the sphygmomanometer 1 in step SB1. When the measurement switch 3B is also operated (step SB1), the CPU 40 executes processing for wrapping the cuff around the body part to be measured. In step SB1, the cuff is wrapped around the body part to be measured by the compression/fixation reel mechanism 81 reeling the wire 81A.

Next, in step SB2, the inflation of the measurement air bladder 13 is started. Then, the processing moves to step SB3.

In step SB3, the CPU 40 determines whether or not the internal pressure of the measurement air bladder 13 has reached a certain pressure in a manner similar to step SA3 and the like. When the CPU 40 determines that the internal pressure of the measurement air bladder 13 has reached the certain pressure, the processing moves to step SB4.

In step SB4, the CPU 40 starts the deflation of the measurement air bladder 13. Then, the processing moves to step SB5. The measurement air bladder 13 can be deflated by opening the valve 22.

Then, the CPU 40 extracts oscillation components associated with volumetric changes in an artery superimposed on the internal pressure of the measurement air bladder 13 during the deflation of the measurement air bladder 13, and calculates blood pressure values using known calculation processing (step SB5).

Thereafter, in step SB6, the CPU 40 determines whether or not calculation of the blood pressure values (a systolic blood pressure value, a diastolic blood pressure value, and/or an average blood pressure value) has been completed. When the CPU 40 determines that calculation of the blood pressure values has been completed, the processing moves to step SB7.

In step SB7, the CPU 40 causes the wire 81A to tighten the measurement air bladder 13 in such a manner that the measurement air bladder 13 is compressed by a force larger than or equal to the atmospheric pressure. More specifically, the CPU 40 drives the motor 82 to cause the wire 81A to operate in the above manner. When a certain time period has elapsed since the start of the process of step SB7, the CPU 40 proceeds to the process of step SB8. The CPU 40 may proceed to the process of step SB8 on the condition that a certain time period has elapsed since the internal pressure of the measurement air bladder 13 reached or fell below a certain value.

In step SB8, the CPU 40 evacuates the air from the measurement air bladder 13 (maintains the state where the valve 22 is left open for a certain time period or longer). Thereafter, the processing moves to step SB10.

In step SB10, the CPU 40 causes the display unit 4 to display the measured blood pressure values and completes the blood pressure measurement processing.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

According to one or more embodiments of the present invention, when the air is evacuated from a measurement air bladder, the evacuation of the air from the measurement air bladder can be facilitated by a compression member applying pressure that is higher than or equal to the atmospheric pressure to the measurement air bladder. This suppresses variations in the amount of the air left in the measurement air bladder at the start of measurement.

As a result, variations in the wrapping strength of a cuff at the start of measurement can be suppressed.

REFERENCE NUMERALS LIST

1 SPHYGMOMANOMETER
2 MAIN BODY
3 OPERATION UNIT
4 DISPLAY UNIT
5 MEASUREMENT MEMBER
6 HOUSING
7 COVER
8 COMPRESSION/FIXATION AIR BLADDER
10 CURLER
13 MEASUREMENT AIR BLADDER
20 MEASUREMENT AIR SYSTEM
21, 31 PUMP
22, 32 VALVE
23, 33 PRESSURE SENSOR
26, 36 PUMP DRIVE CIRCUIT
27, 37 VALVE DRIVE CIRCUIT
30 COMPRESSION/FIXATION AIR SYSTEM
41 MEMORY
81 COMPRESSION/FIXATION REEL MECHANISM
81A WIRE
82 MOTOR
83 MOTOR DRIVE CIRCUIT

The invention claim is:

1. A blood pressure measurement device comprising:
   a measurement air bladder for being wrapped around a body part to be measured;
   a compression air bladder positioned outside the measurement air bladder so as to compress the measurement air bladder from an outside of the measurement air bladder against the body part to be measured;
   a measurement air system that inflates and deflates the measurement air bladder, said measurement air system comprising:
   a first inflation member that inflates the measurement air bladder; and
   a first deflation member that deflates the measurement air bladder;

a compression/fixation air system that inflates and deflates the compression air bladder, said compression/fixation air system being provided independently of the measurement air system, and said compression/fixation air system comprising:
  a second inflation member that inflates the compression air bladder; and
  a second deflation member that deflates the compression air bladder;
a blood pressure determination unit that determines a blood pressure during the inflation by the first inflation member or during the deflation by the first deflation member; and
a control unit that is specifically programmed to cause the compression air bladder to apply a pressure that is higher than or equal to an atmospheric pressure to the measurement air bladder when an internal pressure of the measurement air bladder reaches or falls below a certain pressure due to the deflation by the first deflation member, and
wherein the control unit is specifically programmed to cause the compression air bladder to apply a pressure that is higher than or equal to the atmospheric pressure to the measurement air bladder during the deflation of the measurement air bladder by the first deflation member by controlling the compression/fixation air system.

2. The blood pressure measurement device according to claim 1, wherein the control unit controls a state in which the compression air bladder compresses the measurement air bladder based on a difference between an internal pressure of the measurement air bladder and an internal pressure of the compression air bladder.

3. The blood pressure measurement device according to claim 1, further comprising:
  a flexible member wrapped around the measurement air bladder,
  wherein the flexible member is wrapped around the measurement air bladder in such a manner that a portion of the flexible member overlaps and comes in contact with another portion of the flexible member, and
  wherein the control unit causes the compression air bladder to apply, to the flexible member, a pressure that is higher than or equal to a sum of the atmospheric pressure and a frictional force of the portions of the flexible member that come in contact with each other so as to compress the measurement air bladder.

4. The blood pressure measurement device according to claim 1, wherein the compression air bladder comprises:
  a wrapping member that is wrapped around the measurement air bladder; and
  a reel mechanism that causes the wrapping member to compress the measurement air bladder by reeling the wrapping member.

5. The blood pressure measurement device according to claim 1, wherein the control unit causes the compression air bladder to apply a pressure that is higher than or equal to the atmospheric pressure to the measurement air bladder on a condition that a predetermined time period has elapsed since a start of the deflation by the first deflation member.

* * * * *